United States Patent [19]

Silberstein

[11] Patent Number: 4,955,388

[45] Date of Patent: Sep. 11, 1990

[54] ELECTROENCEPHALOGRAPHIC ATTENTION MONITOR

[75] Inventor: Richard B. Silberstein, Victoria, Australia

[73] Assignee: Swinburne Limited, Victoria, Australia

[21] Appl. No.: 35,610

[22] PCT Filed: Jul. 28, 1986

[86] PCT No.: PCT/AU86/00215

§ 371 Date: Mar. 30, 1987

§ 102(e) Date: Mar. 30, 1987

[87] PCT Pub. No.: WO87/00746

PCT Pub. Date: Feb. 12, 1987

[30] Foreign Application Priority Data

Jul. 30, 1985 [AU] Australia .............................. 01702/85

[51] Int. Cl.$^5$ ........................................... A61B 5/0484
[52] U.S. Cl. ..................................... 128/731; 128/745
[58] Field of Search ............................... 128/731.2, 745

[56] References Cited

U.S. PATENT DOCUMENTS

| | | | |
|---|---|---|---|
| 2,860,627 | 11/1958 | Harden | 128/731 |
| 3,498,287 | 3/1970 | Ertl | 128/731 |
| 3,809,069 | 5/1974 | Bennett | 128/731 |
| 3,855,998 | 12/1974 | Hidalgo-Briceno | 128/745 X |
| 3,901,215 | 8/1975 | John | 128/731 |
| 4,083,365 | 4/1978 | Yancey | 128/731 |
| 4,094,307 | 6/1978 | Young, Jr. | 128/731 |
| 4,140,997 | 2/1979 | Brady | 128/732 |
| 4,201,224 | 5/1980 | John | 128/731 |
| 4,216,781 | 8/1980 | John | 128/731 |
| 4,244,376 | 1/1981 | Fisher et al. | 128/731 |
| 4,304,242 | 12/1981 | Siarkiewicz et al. | 128/745 |
| 4,421,122 | 12/1983 | Duffy | 128/731 |
| 4,493,327 | 1/1985 | Bergelson et al. | 128/731 |
| 4,610,259 | 9/1986 | Cohen et al. | 128/731 |
| 4,632,126 | 12/1986 | Aguilar | 128/732 |
| 4,744,029 | 5/1988 | Raviv et al. | 128/731 X |
| 4,794,533 | 12/1988 | Cohen | 128/731 X |

OTHER PUBLICATIONS

"Prove Evoked Potentials: Theory, Method and Applications," A. Papanicolauo et al., Intern. J. Neuroscience, vol. 24, pp. 107-131 (1984).

Primary Examiner—Angela D. Sykes
Attorney, Agent, or Firm—Wolf, Greenfield & Sacks

[57] ABSTRACT

A method and apparatus for determining the level of attention of a subject to a visual stimulus such as a television commercial displayed on a screen (4) so as to provide objective information for designing the advertising presentation. The technique involves reflecting visible red radiation from arrays (16) of LEDs towards the eyes of the subjects (2) as a control signal at a predetermined frequency. The control signal is first applied to the subjects and EEG responses obtained. The control signal is then simultaneously applied with the display of the television commerical and EEG signals are again obtained. An assessment of the subjects interest is then made by determining the diminution in value of the components of the EEG response attributable to the control signal. A pair of illuminated goggles is also disclosed.

20 Claims, 11 Drawing Sheets

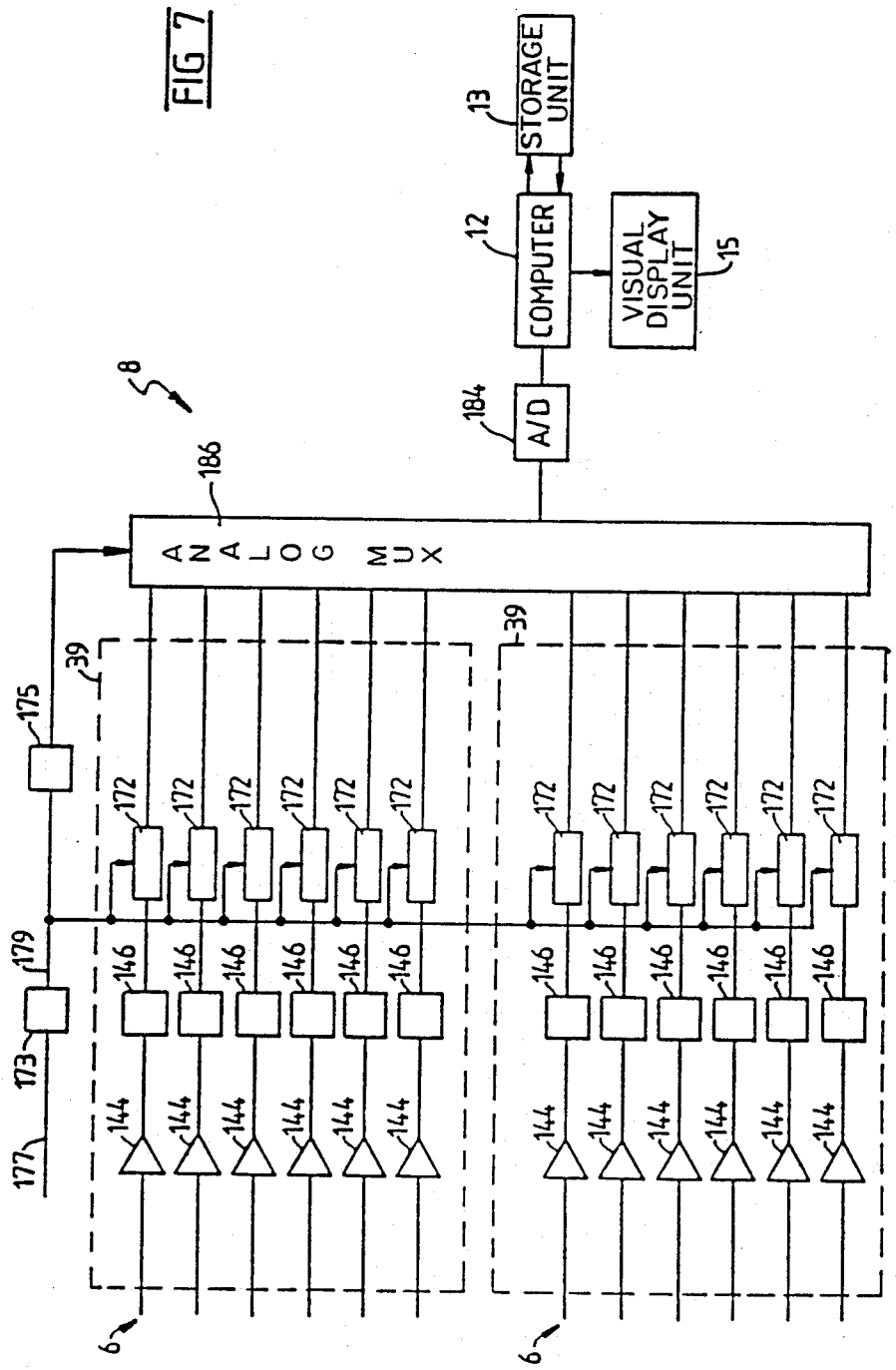

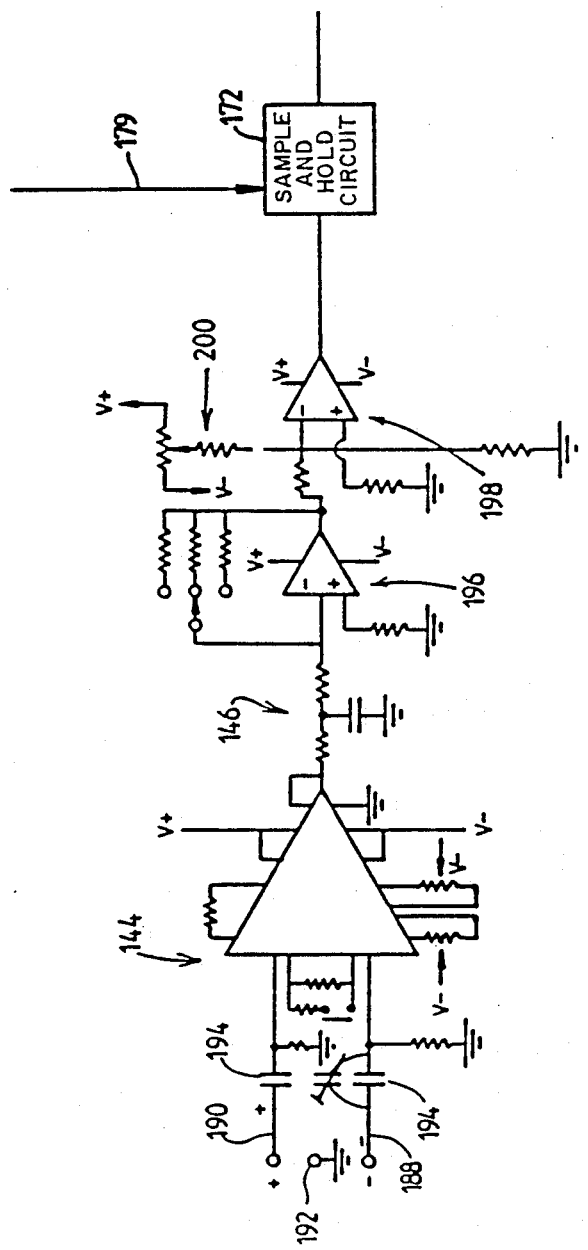

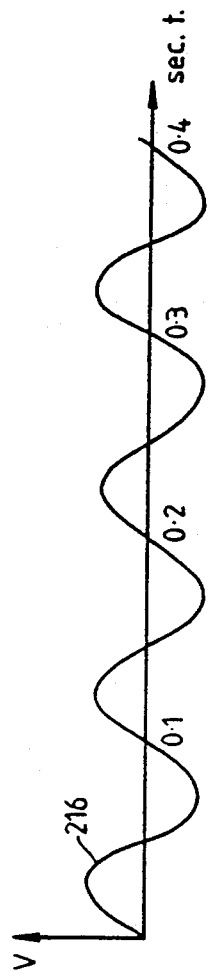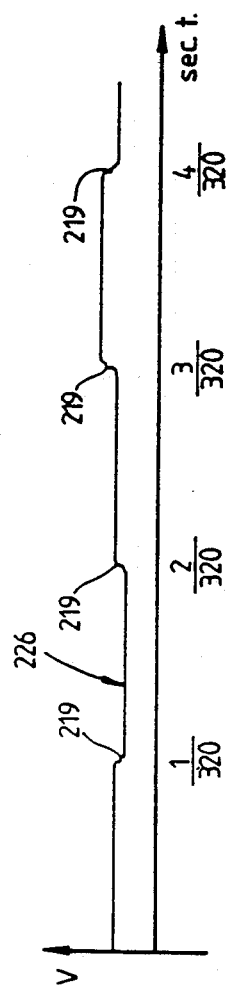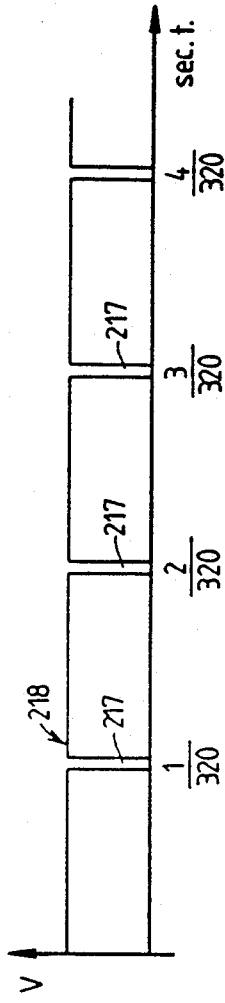

ELECTROENCEPHALOGRAPHIC ATTENTION MONITOR

SUMMARY OF THE INVENTION

This invention relates to an attention monitor.

More particularly, the invention relates to a method and apparatus for monitoring the level of attention of a subject to a visual stimulus. Results from the method and apparatus of the invention provide valuable information of an objective nature as to a subject's attention or interest in visually displayed information such as a television commerical, picture or poster or the like. The assessment can then be used to make changes in the advertisement, picture or poster or the like in order to make it more attractive or more likely to keep the attention of an observer.

According to the present invention there is provided a method of assessing the interest of a subject to a visual stimulus comprising the steps of displaying a visual control signal, obtaining an electroencephalographic (EEG) signal from the subject whilst said visual control signal is being viewed, analysing the EEG signal to determine the magnitude of the component of the EEG signal which corresponds to said control signal, displaying the visual stimulus simultaneously with said control signal, determining the change in the magnitude of said component of the EEG signal, and assessing the interest of the subject by reference to the magnitude of said change.

It has been found that the human brain will discriminate against visual "noise" signals or flicker signals when it is concentrating on other visual information. Accordingly, in the method above, the brain discriminates against the visual control signal which is presented as a visual "noise" signal or a flicker signal and the method of the invention enables accurate assessment of the EEG response to the visual control signal in order to accurately determine the amount by which it has been disminished in amplitude. This provides a measure of the brain's interest in the visual stimulus.

Preferably the visual control signal comprises a signal and the change in magnitude of said component of the EEG signal is determined by using analytical techniques which enable isolation of a sinusoidal component of known frequency from a background signal.

In one form of the invention, the visual stimulus is displayed on a TV screen and the visual control signal is superimposed on the subject's field of view and preferably comprises a visible light signal the intensity of which varies at an accurately known sinusoidal frequency. Alternatively, the control signal may take the form of a visual noise signal or flicker displayed on the television screen. Alternatively, it may comprise a sinusoidal variation of the brightness of the screen. In a further form, a liquid crystal screen could be interposed between the viewer and television screen and be arranged to sinusoidally vary the light transmission therethrough at a fixed sinusoidal rate.

The invention also provides apparatus for assessing the interest of a subject to a visual stimulus comprising means for generating a visually perceptible control signal, display means for displaying a visual stimulus, means for deriving an EEG signal from the subject whilst the visual control signal and the visual stimulus are being simultaneously viewed by the subject, and analysing means for determining the change in magnitude of that component of the EEG signal which is attributable to the control signal from a first state in which the subject views only the controls signal and a second state when the subject views both the control signal and the visual stimulus.

In one arrangement the means for generating a visually perceptible control signal includes a screen interposed between the subject and the display means for adding a component of light or attenuating light transmitted through the screen. For instance, the means for generating may comprise a semi-reflective screen through which the display means is visible and which is arranged to reflect the control signals to the subject. Alternatively, the means for generating a control signal may comprise a liquid crystal screen which is controlled so as to attenuate light passing therethrough.

Alternatively, the display means and means for generating a visually perceptible control signal may be constituted by a single display element, for instance a television screen. In this case, the control signal is superimposed on the visual stimulus which is displayed by the television screen. For instance, the control signal may comprise the periodic intensity of brightness of the screen.

BRIEF DESCRIPTION OF THE DRAWINGS

The invention will now be further described with reference to the accompanying drawings, in which:

FIG. 7 is a more detailed schematic view of the EEG receiving circuitry;

FIG. 8 is a circuit diagram for part of the circuitry of FIG. 7;

FIGS. 9A, B and C, are waveform diagrams useful in understanding the operation of the circuits of FIGS. 7 and 8;

DETAILED DESCRIPTION OF THE PREFERRED EMBODIMENTS

Figure 1:
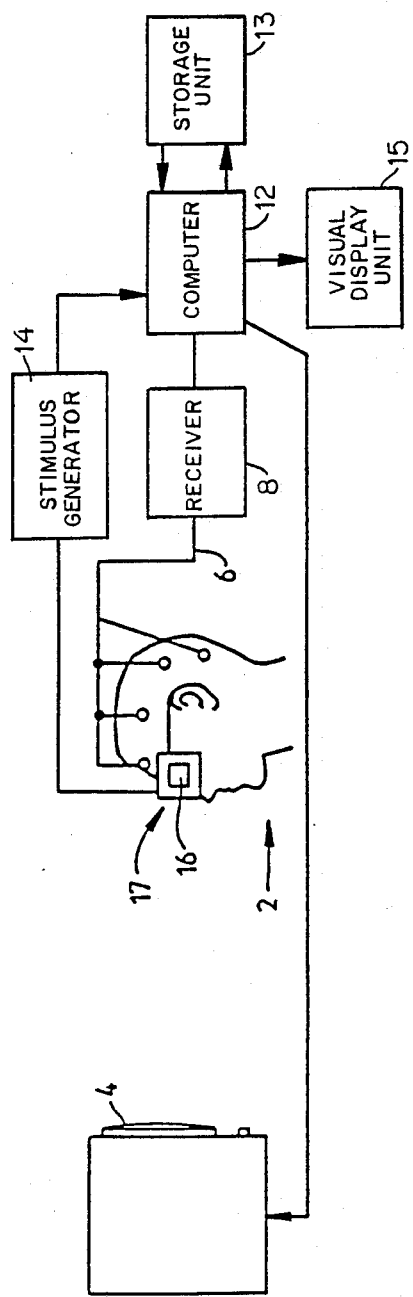
FIG. 1 is a schematic view of an attention monitor for carrying out the invention.

The attention monitor apparatus shown schematically in FIG. 1 is used to determine the interest of a subject 2 in a visual information displayed on a television screen 4. EEG electrodes are applied to the head of a subject and are coupled by input lines 6 to a receiver 8 for amplification and other processing prior to transmission to a computer 12. The computer 12 is coupled to a disc storage unit 13 and a visual display unit 15 and to a printer if required. The apparatus also includes a stimulus generator 14 which applies control signals to left and right LED arrays 16. The LED arrays are preferebly carried by goggles 17 which are worn in use by the user 2. In practice a number of subjects may be provided with goggles 17 for simultaneous testing of the subjects.

Figure 2:
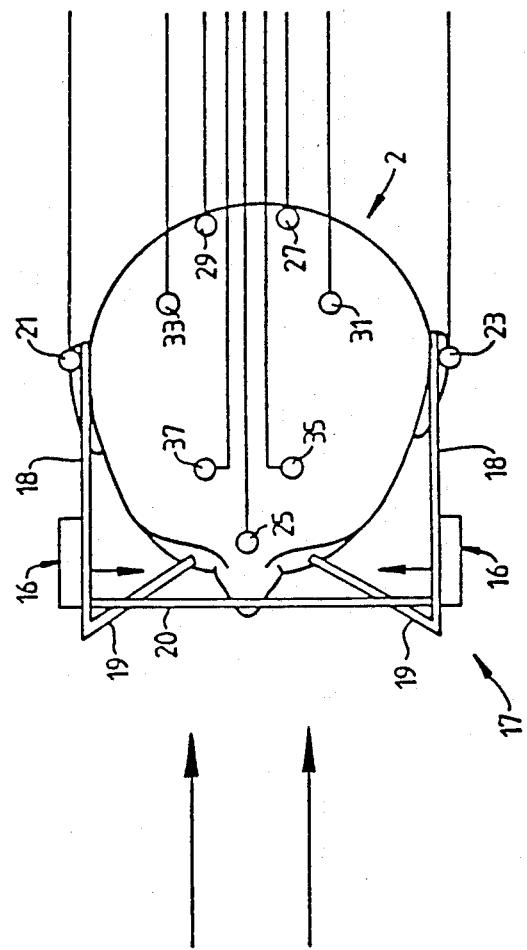
FIG. 2 is a schematic plan view showing the location of EEG electrodes and goggles of the invention.

As shown in FIG. 2, the goggles 17 include arms 18 and cross-piece 20 which enable the goggles to be supported on the ears and nose of the user. Alternatively, a resilient head band could be employed for that purpose. The goggles have a pair of semi-reflective screens 19 which in use are located at about 45° to the line of sight of the user. The screens permit the user to view the television screen 4 directly therethrough and permit light to be reflected towards the eyes of the subject from the left and right LED arrays 16 which are mounted on the arms 18.

Figure 5:
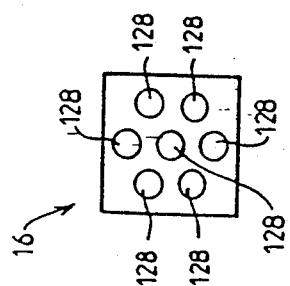
FIG. 5 is a schematic view of an LED array.

FIG. 5 shows schematically the arrangement of one of the LED arrays 16. It comprises seven LED's 128 arranged in a circular pattern. Each array is located within inner and outer shields 138 and 140 to substantially eliminate electric and magnetic fields which might be generated by the currents to the arrays. These stray fields could adversely affect the EEG electrodes on the subject. The conductor 142 to the LED arrays is also shielded for the same reason.

Generally speaking, the operation of the system is as follows: the stimulus generator 14 generates a control signal at a precisely known frequency in the range say 8 to 15 Hz. Preferably the frequency is 10 Hz. The reference frequency is used to modulate the intensity of light output of the LED arrays 16 so that the subject 2 will receive reflected red light from the screens 19 which is modulated in intensity at the reference frequency. Initially, no information displayed on the television screen 4 and EEG signals are obtained for this condition. The receiver 8 and computer 12 are arranged to isolate from the received EEG signals the components which occur at the reference frequency and the magnitude of these components is stored in the disc storage unit 13. This information provides a reference for the subject as to the normal magnitude of EEG signals produced. The system is then operated as before but this time with a visual stimulus applied to the television screen 4. For instance, a television commercial might be screened and the composite EEG signal is received and processed by the receiver 8 and computer 12. The system is arranged to isolate the components of the EEG signal at the reference frequency and to store their magnitudes in the disc storage units 13. The information thus available in the disc storage unit 13 can be used to determine the decrease in magnitude of the component at the reference frequency when the commercial is being screened compared to the case where the commercial is not being screened. The size of the decrease in magnitude is an objective measure of the interest which the subject has in the commercial because the brain of the subject will discriminate against unwanted information when the subject focuses interest on other visual information.

As will be discussed below, the EEG information is sampled comparatively rapidly and all of the sampled information stored in the unit 13. This would enable assessment of different sequences of the commercial displayed on the screen 4. Further, it is envisaged that the commercial displayed on the television screen 4 would be simultaneously viewed by a number, say 25, of subjects so that a reasonable cross-section of likely responses to a commercial can be obtained. It will be appreciated that many variations are possible regarding the number of subjects, the number of commercials or stimuli screened, and the quantity of information stored and also the type of analysis performed on the information so as to make objective determinations of interest in the subject matter being screened.

FIGS. 3 to 11 illustrate in more detail one such arrangement for determination of the interest of a number of subjects to a commercial screened on the television screen 4.

Figure 3:
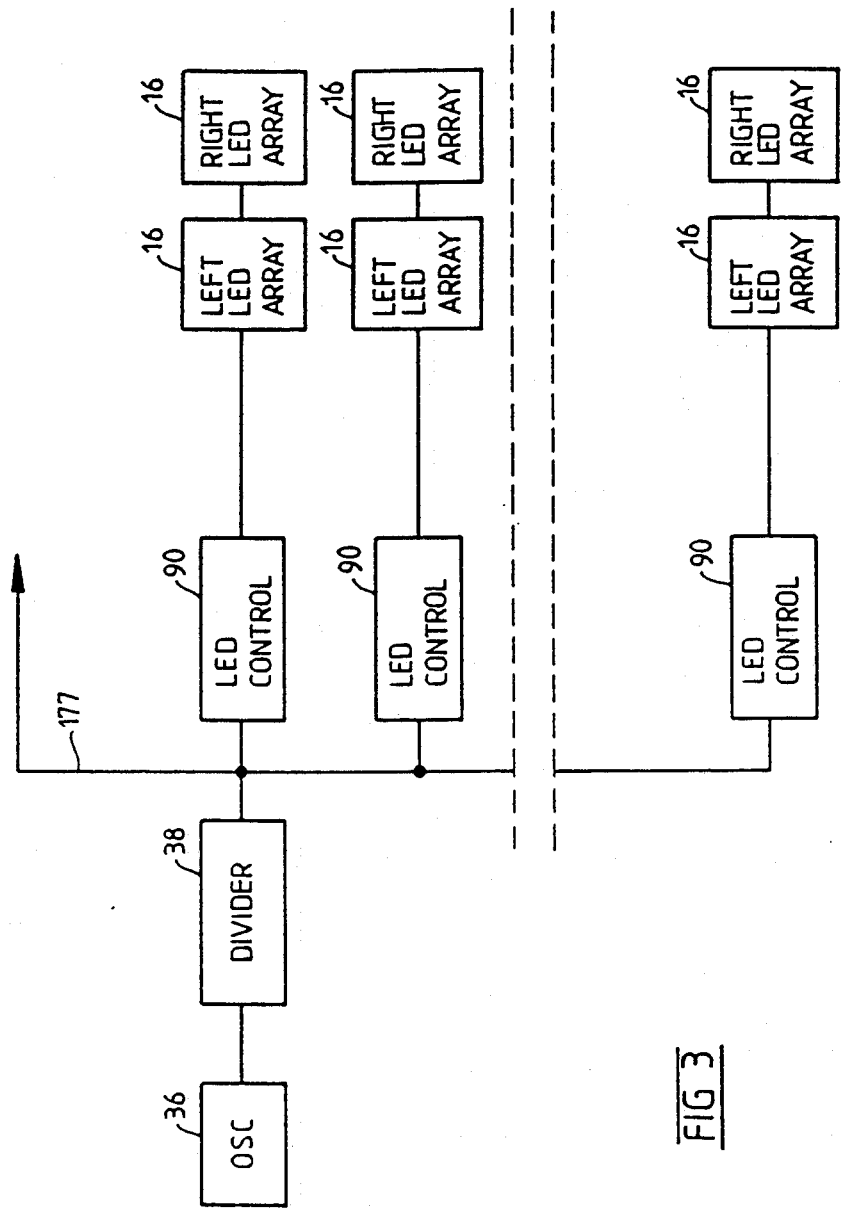
FIG. 3 is a more detailed block diagram of the control signal generator.

FIG. 3 illustrates in more detail the circuitry for the stimulus generator 14. It comprises a crystal controlled oscillator 36 which for instance has a stable frequency at say 4 MHs. Output from the oscillator passes to a divider the output of which is at the reference frequency say in the range 1 to 100 Hz but preferably 10 Hz. The output from the divider 38 is connected to LED control circuits 90, there being one for each set of goggles 17. Output from each circuit 90 then passes to the left and right LED arrays 16 the diodes 128 of which are connected in series.

Figure 4:
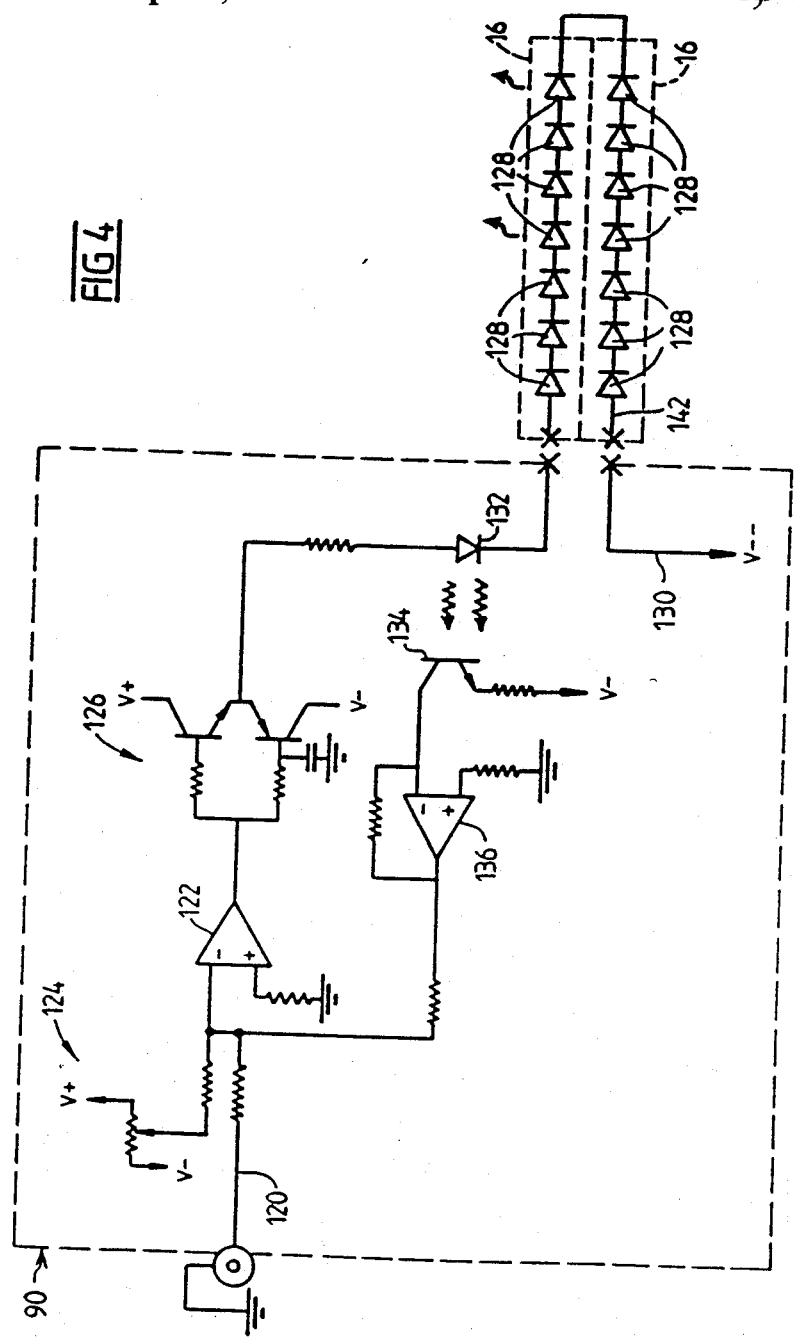
FIG. 4 shows a circuit for controlling the intensity of an LED array.
Figure 6:
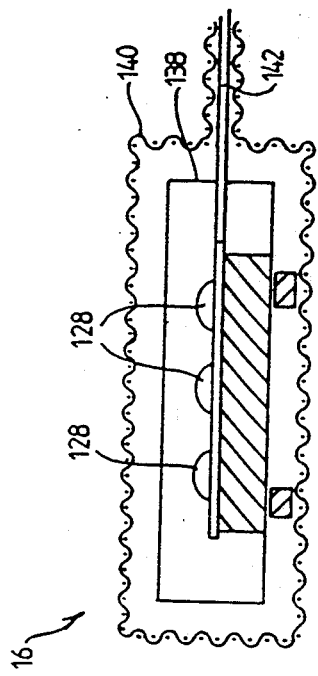
FIG. 6 is a schematic side view of the LED array with shielding.

FIG. 4 shows one circuit realization for the LED control circuit 90. Output from the divider 38 is connected to input line 120 which is coupled to the input of an amplifier 122 via a zero adjusting network 124 which is adjusted so that the output of the circuit 90 has a desired DC level. Output from the amplifier 122 is coupled to the input of a current buffer 126 for driving the LED arrays 16. Each array 16 comprises seven LED devices 128 arranged in a circular pattern, as diagrammatically illustrated in FIG. 45. The fourteen LED's are connected in series and are driven by the currents supplied from the buffer 126. The other end of the series connected of LED's is connected to a negative supply line 130 the value of which is fixed and selected in accordance with the number of LED's connected in series. In order to regulate the intensity of the output of the array 16, a control LED 132 is connected in series and arranged to irradiate a phototransistor 134 the output of which is connected via amplifier 136 to the input of the amplifier 122. The output of the control LED 132 which is selected so as to be of the same type as those used in the array 16 is thus representative of the light intensity output of the array and this is used for negative feedback so as to control the peak intensity reached by the LED arrays 16. The circuit 90 thus ensures the same average level of intensity of light output from the LED arrays 16, regardless of fequency. In one arrangement, it was found convenient to use LED devices manufactured by Stanley known as ESBR diodes. The current flowing through the diodes is typically 20 to 30 milliamps and less than 50 milliamps. The zero adjust circuit ensures that the LED devices are not reversed biased at any stage in the process because this would have the effect of upsetting the otherwise purely sinusoidal inputs to the LED devices. The feedback LED 132 also ensures that the intensity of the light output from the array 16 is a linear function of the current input thereto thereby ensuring that the light emitted by the LED arrays 16 vary in intensity at the reference frequency 10 Hz.

FIG. 2 shows the preferred location of the EEG electrodes for obtaining EEG signals from the subject 2. The arrangement has a pair of electrodes 21 and 23 connected to the ears of the subject. A ground electrode 25 is connected to the forehead of the subject and six other electrodes 27, 29, 31, 33, 35 and 37 are located in accordance with the table below. The code names for the site are in accordance with the International 10–20 Convention. Other sites which may also be used include midway between sites $T_3$ and $T_5$ and midway between sites $T_4$ and $T_6$.

TABLE 1

| ELECTRODE | SITE | |
|---|---|---|
| 27 | $O_1$ | Left occipital site |
| 29 | $O_2$ | Right occipital site |
| 31 | $P_3$ | Left parietal site |
| 33 | $P_4$ | Right parietal site |
| 35 | $F_3$ | Left frontal site |
| 37 | $F_4$ | Right frontal site |
| 25 | $F_{pz}$ | Central forehead as earth |

FIG. 7 shows in more detail the configuration of the receivers 8. It will be seen that each subject 2 has receiver circuitry 39 receiving input from lines 6 from the EEG electrodes. Each receiver circuit 39 has an amplifier 144 for each of the EEG electrodes 27, 29, 31, 33, 35 and 37. The outputs of the amplifiers are coupled to band pass filters 146 which have a pass band in range 1 to 100 Hz. The outputs of the filters 146 are connected to respective sample and hold circuits 172, the outputs of which are connected to an analogue multiplexer 186. The receiver 8 includes a frequency multiplying circuit 173 which has its input from the divider 38 via line 177 and operates to control the sample and hold circuits 172 at a sampling rate which for instance samples the outputs of the filters 146 thirty two times each cycle i.e. 320 times per second. Output line 179 from the multiplier 173 is coupled to a further frequency multiplier 175 which controls the operation of the multiplexer 186 so that output from all of the sample and hold circuits 172 associated with all of the subjects are sequentially transferred to an analogue to digital converter 184 and then to the computer 12.

FIG. 8 shows in more detail the amplifier 144, filter 146 and sample and hold circuit 172 for one of the EEG electrodes say the electrode 27 (as shown in FIG. 2). In this arrangement the ground electrode 25 is connected to the ground input 192 of the amplifier 144. The electrodes 21 and 23 (which are electrically connected together) are connected to the negative input 188 of the amplifier. The electrode 27 is connected to the positive input 190, as shown. The amplifier 144 may comprise a precision instrumentation differential amplifier type AMP-01. The inputs 188 and 190 include coupling capacitors 194 to filter out very low frequency components say below 1 Hz and thus can be regarded as part of the filter 146. Output from the amplifier 144 passes to a resistance—capacitance network which comprises the remainder of the filter 146 and operates to attenuate frequencies above say 100 Hz. Output from the filter 146 is then amplified in the pair of amplifiers 196 and 198, the latter including a DC offset network 200 for adjustment of the DC output level of the output amplifier 198. The output of the amplifier 198 is coupled to the input of the sample and hold circuit 172.

FIG. 9A shows a typical reference waveform of 10 Hz. Waveform 218 shown in FIG. 9C is a suitable waveform for controlling the sample and hold circuits 172. The waveform includes negative pulses 217 which occur at 32 times the rate of the reference waveform 216 (FIGS. 9B and 9C have a different time scale to FIG. 9A). The leading edges of the negative going pulses 217 cause the sample and hold circuit 172 to track the outputs of the filter 146 as indicated by tracked portions 219. The trailing edges 217 of the pulses initiate the start of the holding cycles, as indicated by the waveform 226 of FIG. 9B. The outputs from the sample and hold circuits 172 are transferred to the analogue to digital converter 184 through the multiplexer 186 at a rate controlled by the multiplier 175 whereby all the circuits 172 are sampled and stored in the disk storage unit 13.

Seeing that the reference frequency waveform is precisely known, the programmes within the computer 12 can be arranged to mathematically isolate the components in each of the EEG signals received by the amplifiers 144 which are at the reference frequency by using Fourier analysis techniques. The reference frequency waveform can be applied to the computer 12 directly from the stimulus generator 14 or alternatively it can be pre-programmed into the computer. Generally speaking, for each EEG waveform, $f_{(t)}$, i.e. the output of each sample and hold circuit 172, the output waveform is multiplied by $\sin 2\pi F_1 t$ and by $\cos 2\pi F_1 t$, where $F_1$ is the reference frequency. The sine and cosine products are then integrated over a number of full cycles. This enables the magnitude M to be calculated using the following formula:

$$M = \sqrt{\left[\int_0^{2\pi} f(t) \sin 2\pi F_1 \cdot dt\right]^2 + \left[\int_0^{2\pi} f(t) \cdot \cos 2\pi F_1 \cdot dt\right]^2}$$

The computer 12 however receives digitized versions of the output waveforms 226 of the circuits 172 and therefore digital approximations for the integrals are utilised, as is known in the art of computation.

For each electrode 27, 29, 31, 33, 35 and 37 for each subject, a value for the frequency component at the reference frequency of 10 Hz is first computed whilst there is nothing screened on the television screen 4. This value is referred to as the steady state visually evoked potential SSVEP for each electrode. This value can therefore be used as a reference level against which the corresponding value of the reference frequency component can be compared whilst the commercial is being screened in order to ascertain the diminution in magnitude. One technique for carrying out the computations will now be briefly described with reference to FIG. 10 and FIGS. 11A–11C.

In one example it can be assumed that there are G subjects 2 used to pretest commercials each of which will be displayed three times to the subjects 2 on the television screen 4 in accordance with the following protocol:

1st sequence $B_{11}{}^i$, $C_{11}{}^i$, $B_{12}{}^i$, $C_{12}{}^i$, ... $B_{1p}{}^i$, $C_{1p}{}^i$
2nd sequence $B_{21}{}^i$, $C_{21}{}^i$, $B_{22}{}^i$, $C_{22}{}^i$, ... $B_{2p}{}^i$, $C_{2p}{}^i$
3rd sequence $B_{31}{}^i$, $C_{31}{}^i$, $B_{32}{}^i$, $C_{32}{}^i$, ... $B_{3p}{}^i$, $C_{3p}{}^i$
Where
$B_{11}{}^i$ represents the first blank period (30 sec) of first sequence, with reference to subject i,
$C_{11}{}^i$ represents the first commercial (30 sec) of first sequence, with reference to subject i.

During the recording sequences data is received by the receiver 8, analysed by the computer 12 and stored in the disk unit 13. It can then be analysed in more detail at a later stage.

After gathering the data in the sequences noted above, the computer 12 can then be used to objectively assess the interest of the subjects in the commercials. The first step is the determination of the SSVEP which is determined during the first sequence of blank displays for each subject i.e. during the sequence $B_{11}{}^i$. For convenience the SSVEP for each subject is represented by $F_{1B}{}^g$. The next step is to calculate the normalized mean response for all of the subjects using the following formula:

$$SL(Cij) = \frac{1}{a} \sum_{g=1}^{a} \frac{SL^g(Cij)}{F^g_{1B}}$$

where $SL^g(Cij)$ = slice of EEG data recorded during display of the Jth commercial in the ith sequence for subject g.

The next step involves determining the magnitude of the EEG response at the reference frequency for each electrode site and each commercial whilst the commercial is being displayed and subtracting the normalized mean response therefrom so as to obtain the change in magnitude which can be therefore attributed to the interest of the subjects in the commercial being screened.

Figure 10:
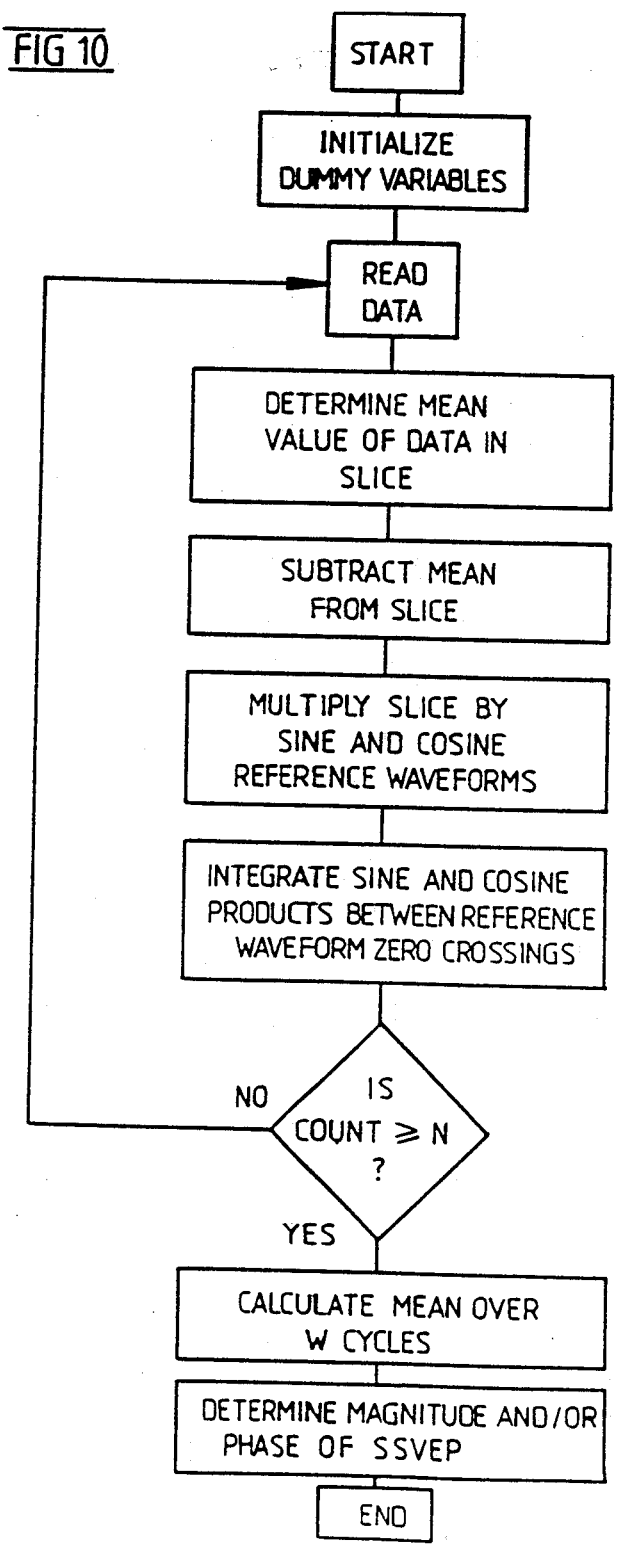
FIG. 10 is a flowchart showing the method of calculating steady state visually evoked potential (SSVEP)
Figure 11A:
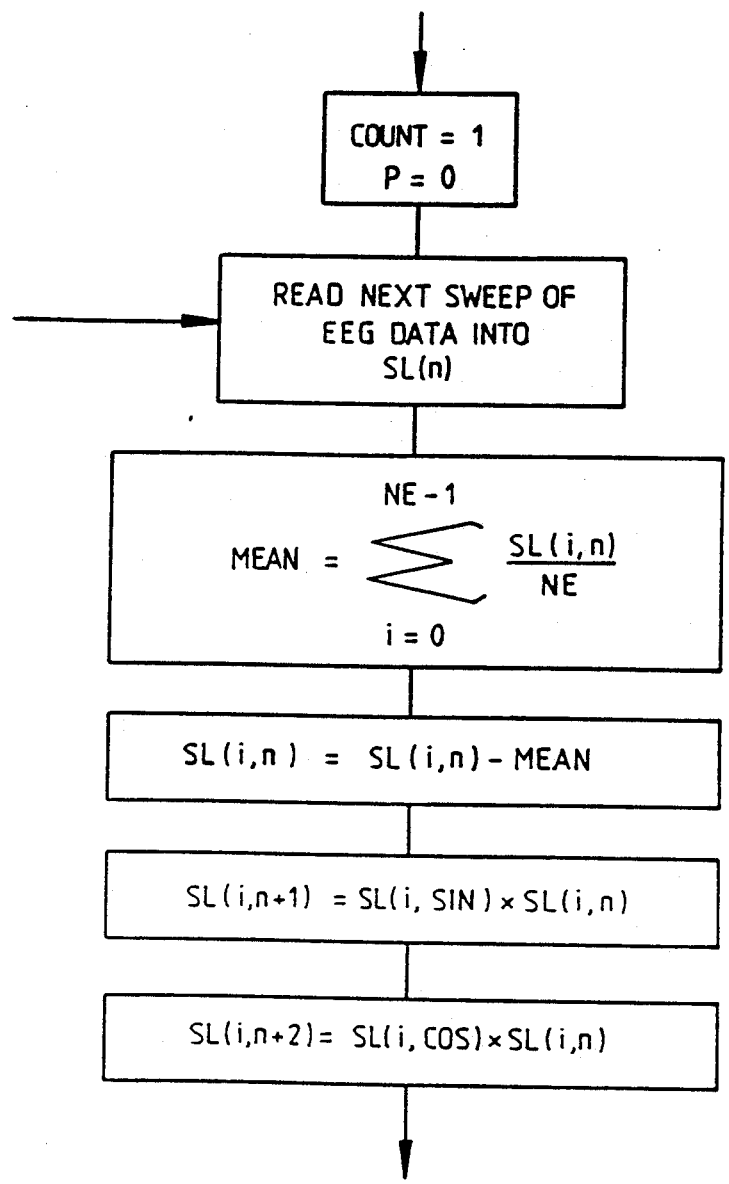
FIGS. 11A, B and C show more detailed parts of the chart of FIG. 10.
Figure 11B:
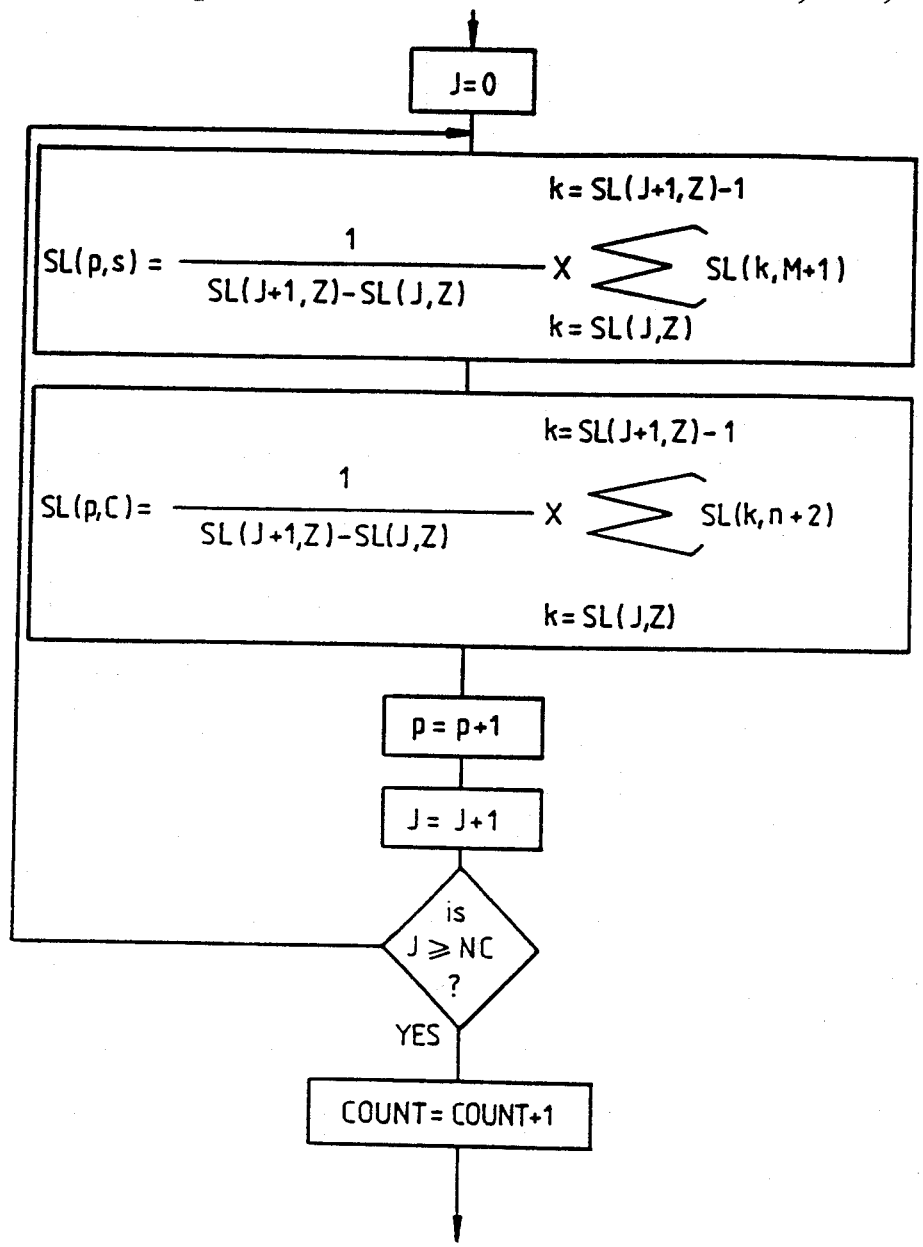
Figure 11C:
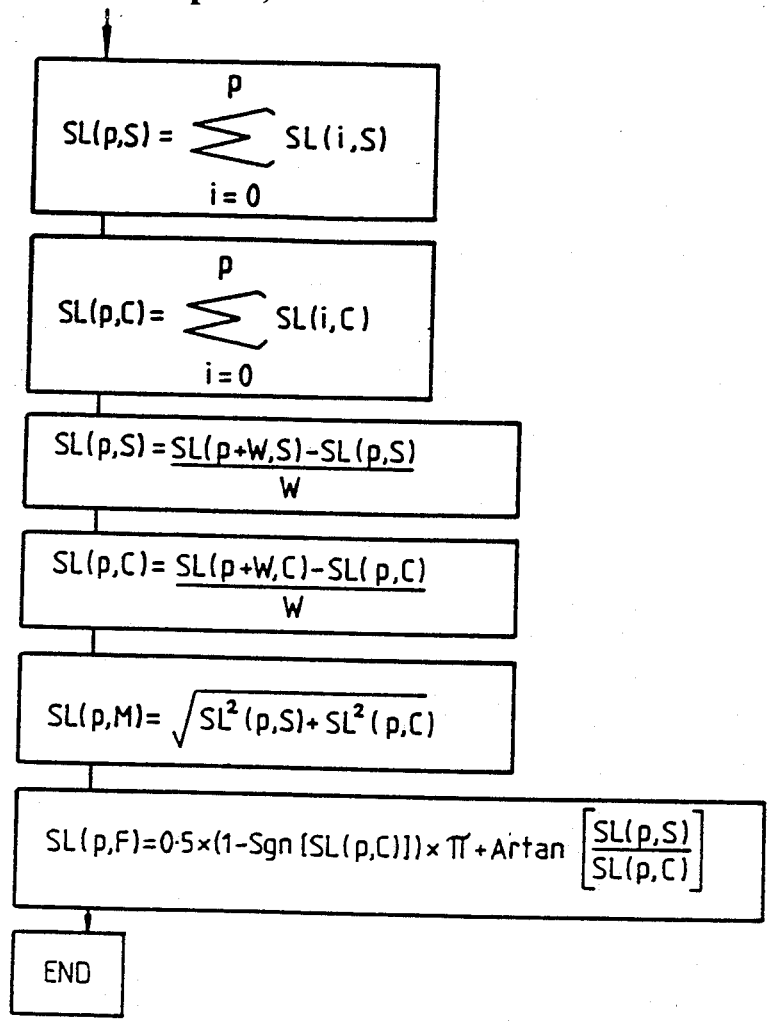

FIG. 10 represents in diagrammatic form a flow-chart for evaluating the SSVEP magnitude for N slices of EEG data from a particular EEG electrode recording site. FIGS. 11A, B and C show in more detail the steps of the flowchart of FIG. 10.

The following terms and parameters are used in the flowcharts:

SL—an array of numbers stored in the disk unit 13 (usually 512, 1024 or 2048) and referred to as a "slice".
NE—The number of elements in a slice.
$SL^g$—slice associated with subject g
SL(n)—nth slice
SL(i,n)—ith point of slice n
$SL^g(B_{ij})$—slice of EEG data recorded during viewing of the Jth blank period in ith sequence for subject g.
SL(SIN)—slice with sine reference waveform
SL(COS)—slice with cosine reference waveform
NC = number of complete cycles of reference waveform (10 Hz) in slice duration, typically NC = 25 cycles.
SL(z)—slice with locations of positive gradient zero crossings of sine reference waveforms.
SL(m) = slice with magnitude of SSVEP as a function of time.
SL(F) = slice with phase of SSVEP as a function of time.

The information yielded by the analysis used above can be used as an objective assessment of the interest of the various subjects in the commercials being screened. Further, it is possible to look at say 10 second segements of each commercial in order to ascertain the viewer's interest in that segment so that useful information can be obtained regarding the reaction to different parts of the commercial. It follows of course that the information obtained can be used to change the commercial and thereby produce a more commercially useful end product. It is also possible to discriminate different types of evoked reaction by considering outputs generated from different EEG electrode sites on the subjects. Information of this sort is of course useful when a particular effect is intended in a commerical.

Many modifications will be apparent to those skilled in the art without departing from the spirit and scope of the invention.

I claim:

1. A method of assessing the interest of a subject in a visual stimulus, by means of application of a control signal is combination with said visual stimulus, which control signal produces a distinguishable response in the subject, and measurement of said interest by reference to a change in said response, said method comrpising the steps of
displaying a periodic visual control signal having a preselected frequency,
obtaining an electroencephalographic (EEG) signal from the subject whilst said visual control signal is being viewed, and
analysing the EEG signal to determine the magnitude of that component of the EEG signal which corresponds in frequency to said control signal,
wherein said method further comprises the steps of displaying said control signal and the visual stimulus simultaneously to the subject,
obtaining and analysing the EEG signal to determine the magnitude of said component during said simultaneous display,
determining the change in the magnitude of said component of the EEG signal, and
assessing the interest of the subject in said visual stimulus in accordance with said change.

2. A method as claimed in claim 1, wherein the visual control signal comprises a simusoidal signal (216).

3. A method as claimed in claim 2, wherein the visual control signal is a red signal which is varied in intensity.

4. A method as claimed in claim 1, wherein a semi-reflective screen (19) is placed between the subject and a source of said visual stimulus and the visual control signal is reflected towards the eye or eyes of the subject.

5. A method as claimed in claim 4 wherein said visual stimulus is displayed oh a television screen (4).

6. A method as claimed in claim 5 wherein the visual stimulus is an advertising material.

7. A method as claimed in claim 6 wherein the advertising material is altered and displayed in order to attain a higher level of interest in the subject.

8. A method as claimed in claim 6 wherein the advertising material is simultaneously displayed to a plurality of subjects and the individual responses are averaged.

9. A method as claimed in claim 1, wherein the method is repeated with respect to each of a plurality of subjects, and said change in magnitude for each subject is determined indirectly by the steps of:
calculating a normalized mean response from the magnitudes of said component of the EEG signal determined for display of the control signal alone to each of the individual subjects; and
subtracting the normalized mean response from the magnitude of said component of the EEG signal determined for display of the control signal and the visual stimulus simultaneously to each of the subjects respectively.

10. Apparatus for assessing the interest of a subject in a visual stimulus by means of application of a control signal in combination with said visual stimulus, which control signal produces a distinguishable response in the subject, and measurement of said interest by reference to a change in said response, comprising means for generating a visually perceptible periodic control signal having a predetermined frequency,
display means for displaying a visual stimulus,
means for deriving an EEG signal from the subject whilst the visual control signal and the visual stimulus are being simultaneously viewed by the subject, and
analysing means for determining the change in magnitude of that component of the EEG signal which is attributable to the periodic control signal from one state in which the subject views only the control signal and another state when the subject views both the control signal and the visual stimulus, the analysing means including discriminating means for discriminating against components of the EEG signal which are not at said predetermined frequency.

11. Apparatus as claimed in claim 10, wherein the means for generating a visually perceptible signal comprises a source of red radiation and means for sinusoidally varying the intensity of the radiation at the predetermined frequency.

12. Apparatus as claimed in claim 10 wherein said frequency is in the range 1 to 100 Hz.

13. Apparatus as claimed in claim 12 wherein said frequency is approximately 10 Hz.

14. Apparatus as claimed in claim 10 wherein said means for generating a visually perceptible signal comprises an array (16) of LEDs.

15. Apparatus as claimed in claim 14 wherein the LED arrays are mounted upon spectacle frames (18).

16. Apparatus as claimed in claim 15 wherein the display means comprises a television screen (4) and wherein the spectacle frames include semi-reflective screens (19) which permit the subject to view the television screen directly, the screens reflecting radiation from the LED arrays towards the eye or eyes of the subject.

17. Apparatus as claimed in claim 10 wherein the discriminating means includes a sample and hold curcuit (172) which holds the output value of said EEG signal at the end of each period of the frequency component of the stimulus.

18. Apparatus as claimed in claim 10 wherein the discriminating means includes an arithmetic unit (12) for calculating the magnitude $M_n$ of the EEG signal at said frequency by taking the square root of the sum of the squares of said output values.

19. Apparatus as claimed in claim 10, which further comprises a device for use in assessing the interest of a subject in visual stimulus, said device comprising support means (18, 20) for supporting at least one semi-reflective screen (19) adjacent to at least one of the eyes of a subject whereby the subject can view directly the visual stimulus, and a source (16) of visible radiation carried by the support means for reflecting radiation from said source towards the eye or eyes of the subject so as to provide the visual control signal.

20. Apparatus as claimed in claim 10, wherein the analyzing means comprises means for calculating a normalized mean response from the responses of each of a plurality of subjects to the control signal alone, and for determining said change in magnitude for each subject by subtracting the normalized mean response from the magnitude of said component of the EEG signal determined for each subject for simultaneous display of the control signal and the visual stimulus.

* * * * *

UNITED STATES PATENT AND TRADEMARK OFFICE
CERTIFICATE OF CORRECTION

PATENT NO. : 4,955,388
DATED : September 11, 1990
INVENTOR(S) : Silberstein

It is certified that error appears in the above—identified patent and that said Letters Patent is hereby corrected as shown below:

Col. 4, line 10 - change "MHs" to -- MHz --.

Col. 4, line 30 - change "connected" to -- connection --.

Col. 6, line 2 - change "filter" to -- filters --.

Col. 8, line 12 - change "comrpising" to -- comprising --.

Col. , line -

Signed and Sealed this

Twenty-eighth Day of April, 1992

Attest:

HARRY F. MANBECK, JR.

Attesting Officer     Commissioner of Patents and Trademarks